(12) United States Patent
Morrissey et al.

(10) Patent No.: US 8,545,497 B2
(45) Date of Patent: Oct. 1, 2013

(54) APPARATUS FOR USE IN THE PROPHYLAXIS OR TREATMENT OF TISSUE

(75) Inventors: Anthony Morrissey, Blarney (IE); Declan Soden, Passage West (IE); Gerald O'Sullivan, Bishopstown (IE); Christopher Collins, Ashington (IE); Colum Dunne, Clonmel (IE); John Piggott, Ballsbridge (IE); Denton A. M Prior, Isle of Skye (GB); Andrew Watson, Isle of Skye (GB); Peter McGeehin, Newbury (GB)

(73) Assignee: University College Cork—National University of Ireland, Cork, Cork (IE)

( * ) Notice: Subject to any disclaimer, the term of this patent is extended or adjusted under 35 U.S.C. 154(b) by 1588 days.

(21) Appl. No.: 11/525,204

(22) Filed: Sep. 22, 2006

(65) Prior Publication Data
US 2007/0179535 A1    Aug. 2, 2007

Related U.S. Application Data

(63) Continuation of application No. PCT/IE2005/000030, filed on Mar. 24, 2004.

(30) Foreign Application Priority Data

Mar. 25, 2004   (GB) .................................. 0406709.6
May 27, 2004    (GB) .................................. 0411934.3

(51) Int. Cl.
*A61B 18/18*    (2006.01)
(52) U.S. Cl.
USPC .............................................. 606/45; 606/41

(58) Field of Classification Search
USPC ....................................................... 606/41–45
See application file for complete search history.

(56) References Cited

U.S. PATENT DOCUMENTS

| | | | |
|---|---|---|---|
| 3,674,031 A | 7/1972 | Weiche | 128/303 |
| 4,130,112 A | 12/1978 | Frazer | 128/2 |
| 4,587,958 A | 5/1986 | Noguchi et al. | 128/24 |
| 5,123,902 A | 6/1992 | Mueller et al. | 604/21 |
| 5,137,817 A | 8/1992 | Busta et al. | |
| 5,277,696 A | 1/1994 | Hagen | 606/49 |
| 5,295,955 A | 3/1994 | Rosen et al. | 604/22 |
| 5,422,272 A | 6/1995 | Papp et al. | |
| 5,704,908 A | 1/1998 | Hofmann et al. | |
| 5,810,806 A | 9/1998 | Ritchart et al. | |
| 6,014,584 A * | 1/2000 | Hofmann et al. | 604/21 |
| 6,022,316 A | 2/2000 | Eppstein et al. | |
| 6,500,141 B1 | 12/2002 | Irion et al. | |

(Continued)

FOREIGN PATENT DOCUMENTS

| | | |
|---|---|---|
| EP | 102877 | 8/2000 |
| WO | WO 00/00250 | 1/2000 |

(Continued)

*Primary Examiner* — Linda Dvorak
*Assistant Examiner* — Amanda Scott
(74) *Attorney, Agent, or Firm* — Jacobson Holman PLLC

(57) ABSTRACT

Apparatus (20) for carrying out a prophylactic or treatment procedure on tissue comprises a device (21) having a chamber (22) and at least one active element such as an electrode (23) within the chamber (22). The chamber (22) has an opening (26) through which tissue is drawn into the chamber (22). Means for drawing the tissue into the chamber may comprise a vacuum lumen with vacuum orifices (25) in the chamber (22). Treatment such as electroporation may be applied to tissue in the chamber (22).

27 Claims, 13 Drawing Sheets

(56) References Cited

U.S. PATENT DOCUMENTS

| | | |
|---|---|---|
| 6,520,950 B1 | 2/2003 | Hofmann et al. |
| 6,558,382 B2 * | 5/2003 | Jahns et al. ............ 606/41 |
| 6,790,214 B2 | 9/2004 | Kraemer et al. |
| 6,852,108 B2 | 2/2005 | Barry et al. |
| 2002/0173688 A1 | 11/2002 | Chen et al. |
| 2003/0149407 A1 | 8/2003 | DiResta et al. |
| 2003/0216730 A1 * | 11/2003 | Barry et al. ............ 606/45 |

FOREIGN PATENT DOCUMENTS

| | | |
|---|---|---|
| WO | WO 00/23143 | 4/2000 |
| WO | WO 00/35533 | 6/2000 |
| WO | WO 00/56395 | 9/2000 |
| WO | WO 00/67837 | 11/2000 |
| WO | WO 03/013615 | 2/2003 |

\* cited by examiner

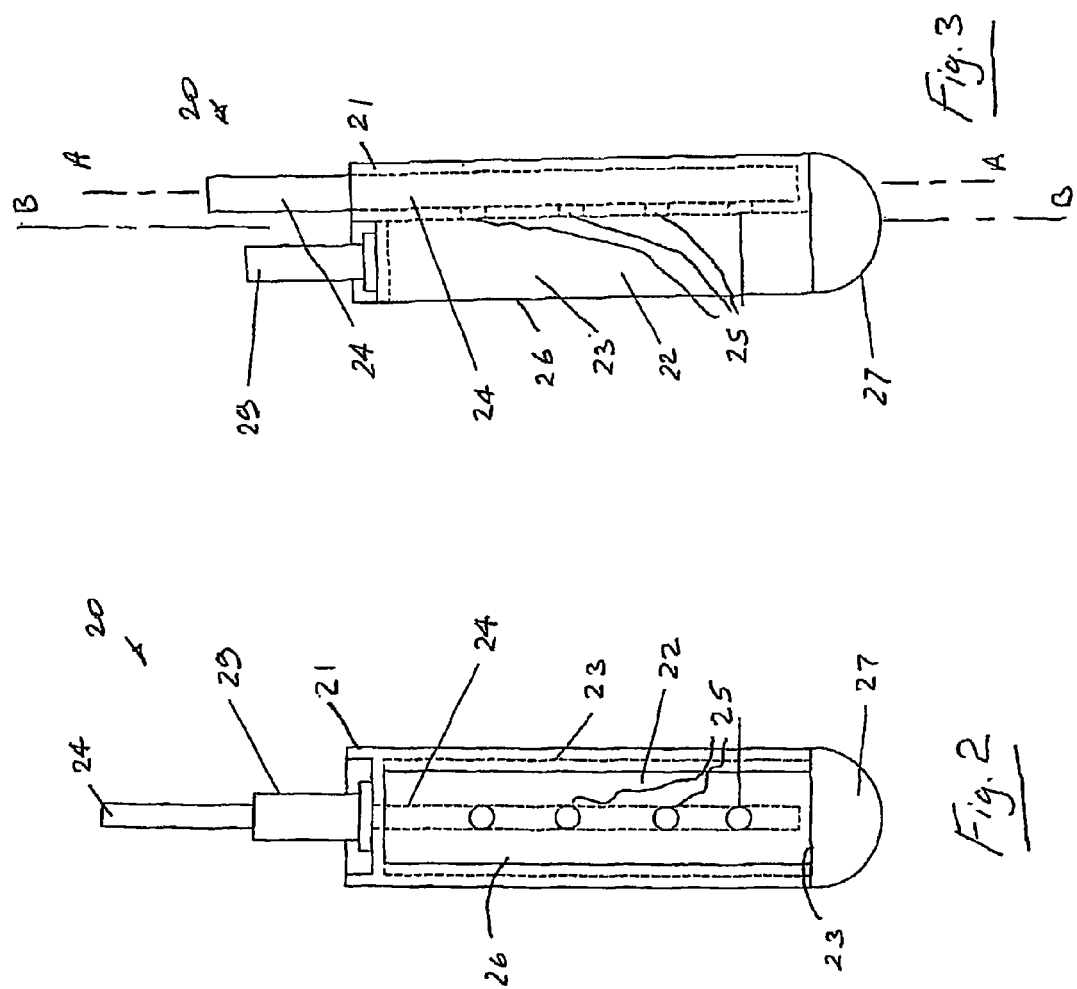

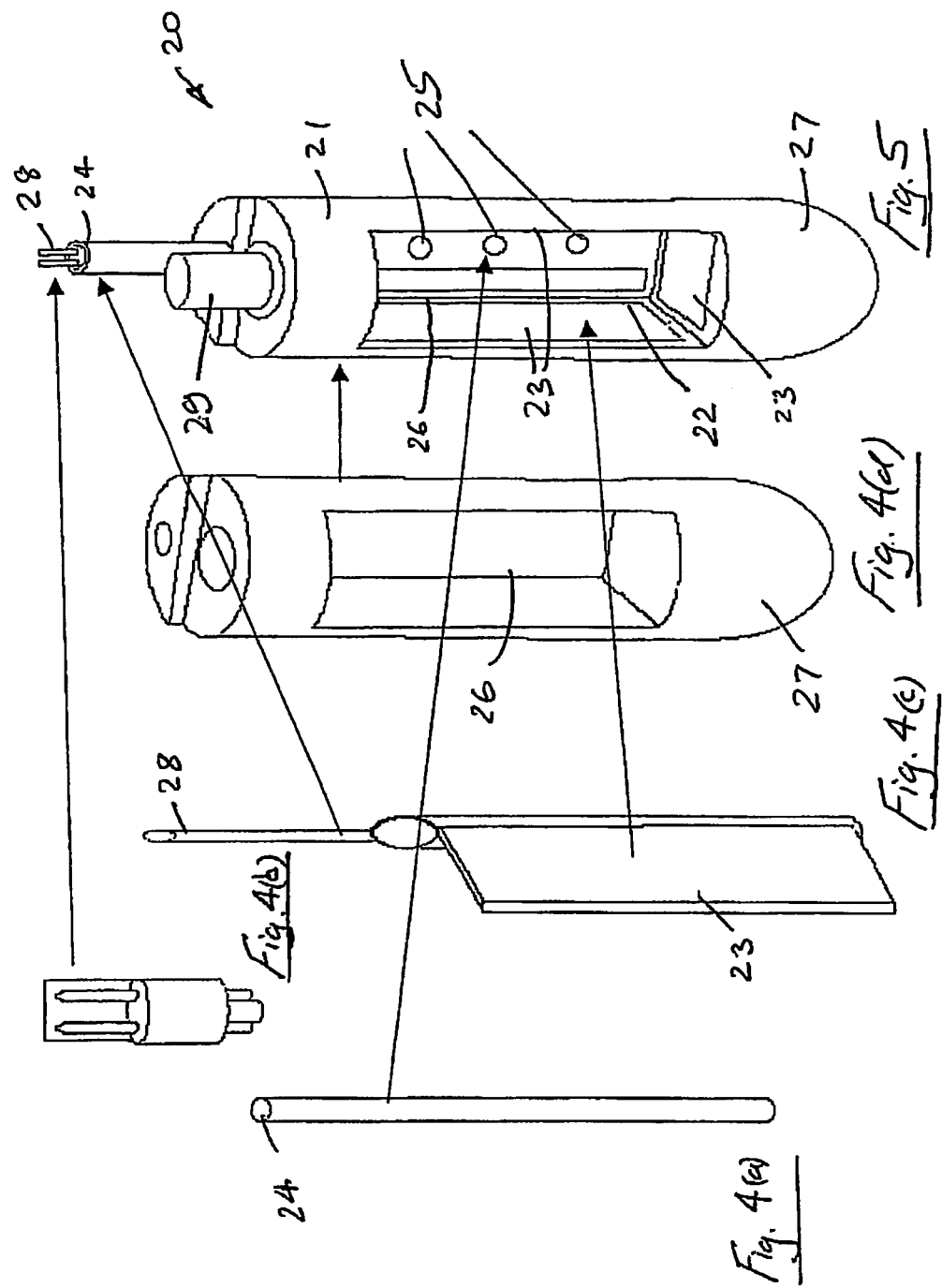

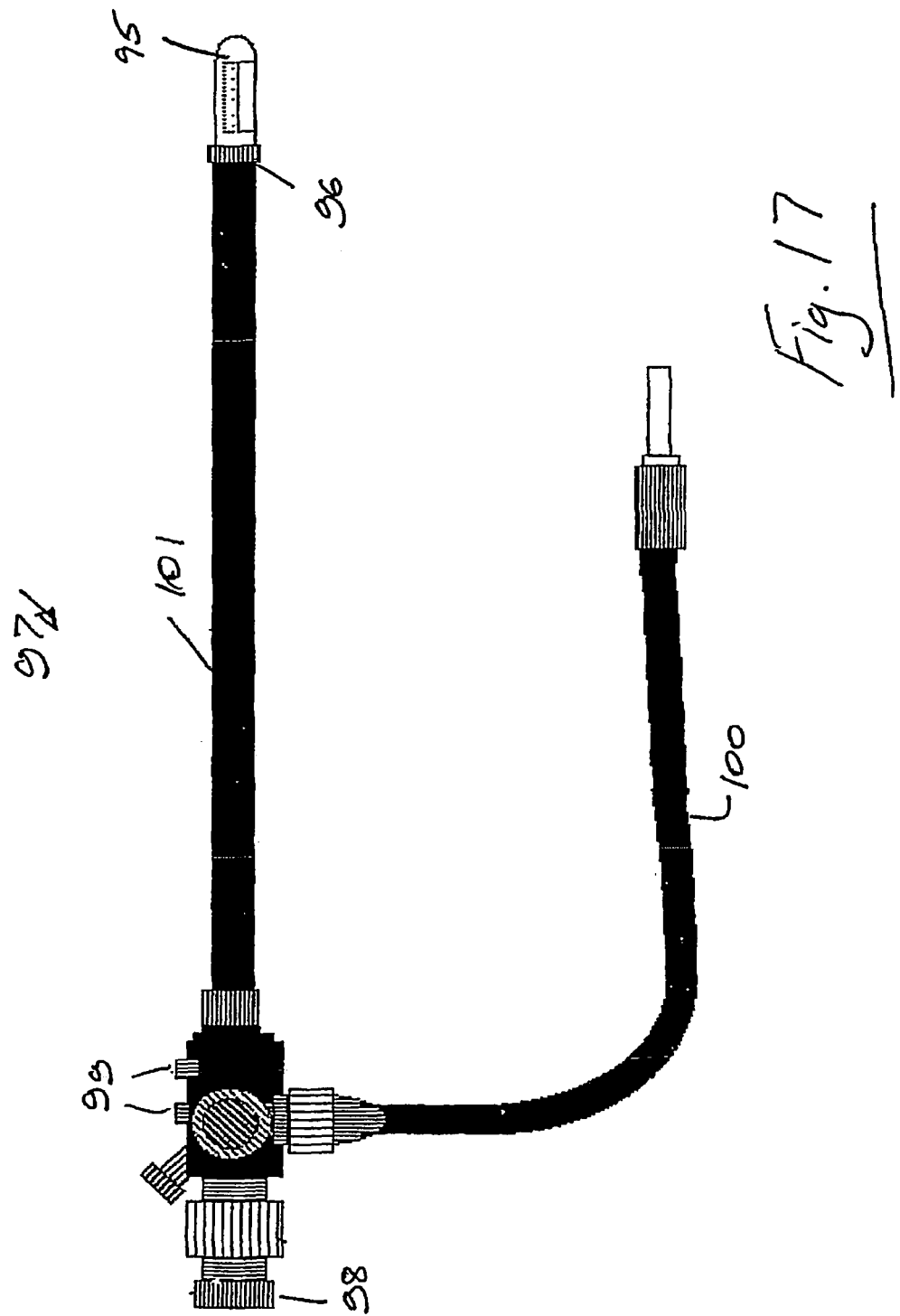

APPARATUS FOR USE IN THE PROPHYLAXIS OR TREATMENT OF TISSUE

This is a continuation of PCT/IE05/000030 filed Mar. 24, 2004 and published in English.

INTRODUCTION

This invention relates to an apparatus for carrying out a prophylactic or treatment procedure on tissue, and to a method of prophylaxis or treatment of tissue.

Cancers or otherwise diseased tissue in or on the inner surface of the hollow viscera, such as the oesophagus or bowel, are generally visually and surgically accessible with a conventional endoscope. Laparoscopy is a surgical technique for accessing body cavities through a small incision, known as a laporotomy, typically through the abdominal wall. The laparoscope is a type of endoscope with various surgical tools and adaptors, with a diameter of ~10 mm and length of ~300 mm, shorter than the flexible devices required for the hollow viscera. The laparoscope allows access to organs in the abdomen, including the bowel, liver, stomach, pancreas, spleen and ovaries. The laparoscope can also be used in the chest, when it is known as a thoracoscope, allowing access to the lungs. The same principle applies to bladder and prostate which are accessible through a rigid endoscope, when it is known as a ureteroscope, albeit with different (smaller) dimensions.

In the more advanced western economies cancers in the organs accessible with these devices represent the greater fraction of cancers commonly encountered. Furthermore, the use of endoscopic techniques in surgery is increasing because they are minimally invasive, safer and reduce significantly the in-hospital treatment and recuperation periods.

Surgical treatment strategies for cancers often include a follow-up period of chemotherapy, although sometimes chemotherapy is the only method used. The term chemotherapy is here used in the most generic sense, and is taken to include the use of medicines, medicinal products, therapeutic agents and other chemical species as in, for example and not limited to, gene therapy and the various sub-classes of this therapy. Techniques are employed that improve the efficacy of chemotherapy by essentially physical means. These include photo-dynamic therapy (PDT), when a drug is activated or enhanced in effect by the absorption of light, sonophoresis, acoustic or ultrasonic fields and by the application of a uniform or pulsed electric field so that a medicinal product—typically of genetic material that does not easily enter tumour cells—is encouraged to enter cells by the temporary breakdown of cell walls. Therapeutic "electroporation" involves application of electric fields to target cells/tissues, thereby rendering their cell membranes transiently porous, thus making feasible the cellular uptake and efficacy of previously impermeant and ineffective therapeutic agents. Electroporation is a physiological phenomenon that occurs in cell membranes as cells are exposed to electrical fields of sufficiently high intensity. Under such conditions, a high trans-membrane voltage is induced causing changes in the membrane and resulting in enhanced cell membrane permeability. Molecules, such as some drugs or nucleic acids, which are otherwise unable to cross the cell membrane, due to electroporation, can enter the cells. Electroporation is the basis for electrochemotherapy and electrogenetherapy. In these combined therapies, the electrically-induced cell membrane permeabilization is exploited to deliver anticancer drugs (electrochemotherapy) or genes (electrogenetherapy) directly into the cells. Molecules with intrinsically high activity, such as some anticancer drugs or DNA/RNA molecules, enter the cells in sufficiently large quantities to effectively influence targets within the cells. Radiation therapy is a physico-chemical technique that can be used alone or in conjunction with a chemical agent that acts, for example, as a selective absorber or to activate a precursor to an efficacious substance created in-situ. These techniques can also be used in combination, an illustrative example being ultrasonic enhancement of an applied pulsed electric field. Other combinations are possible and need not be limited to two impressed fields.

In the case of PDT the tissue or tumour is illuminated with radiation in or close to the visible spectrum and the tumour or tissue need not necessarily be contacted by the means of radiation transmission but if direct contact is not achieved the light intensity can still be tailored precisely by the use of both refractive and reflective rigid elements. In the case of the other physical enhancement methods the tumour or tissue is generally brought into physical contact or close proximity with rigid elements that are typically metallic conductors or radiation sources that are generally solids though not necessarily metallic. Radiation sources can be considered to be active in a sense analogous to electrodes or transmissive elements used for the other enhancement methods. The elements in contact or close proximity with the tissue that bring about the enhancement of the treatment process—whether electrodes, optical elements or radiation sources—are hereafter described by the term 'active elements'. These active elements can be impregnated with therapeutic agents that are given up to the tissue when in contact with it. This transfer can be further enhanced by the application of a physical enhancement process, or more than one such process in combination.

With most of these physically-based enhancement techniques, difficulties frequently arise in endoscopic implementations. Absence of uniformity in the physical field being applied often occurs which causes variations in the degree of treatment given to different regions of the diseased or cancerous tissue, typically some regions being over-treated and other regions being under-treated.

This invention is therefore aimed at addressing at least some of the difficulties of conventional approaches.

STATEMENTS OF INVENTION

According to the invention there is provided apparatus for carrying out a prophylactic or treatment procedure on tissue comprising:
  a device having a chamber and at least one active element within the chamber;
  means for drawing tissue into the chamber; and
  means for applying a treatment to tissue drawn into the chamber.

In one embodiment the chamber has an opening through which tissue is drawn into the chamber. The opening may be at a side of the chamber. The opening may be at an end of the chamber.

In one case the means for drawing tissue into the chamber comprises means for applying a vacuum to tissue. The apparatus may comprise a vacuum lumen for connecting the chamber in communication with a vacuum source. The apparatus may comprise one or more vacuum orifices for connecting the vacuum lumen in communication with the chamber.

In one embodiment the vacuum source is configured to be located externally of a body.

In one case the longitudinal axis of the vacuum lumen is offset radially from the longitudinal axis of the chamber.

In one embodiment the means for drawing tissue into the chamber is configured to draw tissue towards the active element. The means for drawing tissue into the chamber may be configured to draw tissue into contact with the active element.

In one embodiment the device is configured to define a smooth crossing profile. A distal end of the device may be substantially rounded.

In one case the active element comprises an electrode. The means for applying treatment may comprise means for applying electroporation to tissue in the chamber.

In one embodiment the active element comprises a conductive element.

The active element may comprise an optical element.

Alternatively or additionally the active element comprises a radiation source.

The active element may alternatively or additionally comprise an ultrasound source.

In one case the apparatus comprises at least two active elements. At least some of the active elements may be the same.

At least some of the active elements may be different.

In one embodiment at least one active element has a therapeutic agent associated therewith. For example, the active element may be impregnated with a therapeutic agent.

In one arrangement the location of the active elements in the chamber is configured to minimise the variation in intensity of the physical field within the chamber.

In one embodiment the chamber comprises a plurality of openings.

In one embodiment the device has means for receiving a treatment device such as an injector, needle or the like.

The apparatus may comprise at least one sensor. The sensor may be used to monitor the treatment procedure. The sensor may be provided integral with the active element.

In one embodiment the device has at least one port to facilitate coupling of one or more ancillary devices such as laparoscopic devices to the device.

The port may be configured to facilitate coupling of the ancillary laparoscopic device to the device with the ancillary device being optionally aligned with the chamber.

In one case the ancillary device comprises an endoscope for transmitting visual information, and/or a needle for injecting a therapeutic agent into tissue.

In one embodiment the device is adapted for mounting to an instrument. The device may be adapted for mounting to a distal end of an instrument. The instrument may comprise an endoscope, a laparoscope, a thoracoscope or a ureteroscope.

The instrument may comprise a catheter.

In one embodiment the apparatus comprises a connector lumen for connecting the active element and/or the sensor in communication with a controller. The controller may be configured to be located externally of a body.

The invention also provides an instrument, an endoscope, a laparoscope, a thoracoscope, a ureteroscope, or a catheter comprising an apparatus of the invention.

In another aspect the invention provides a method of prophylaxis or treatment of tissue comprising the steps of:
providing a device having a chamber and at least one active element within the chamber;
delivering the device to a site of interest;
drawing tissue into the chamber;
applying treatment to the tissue drawn into the chamber using the at least one active element within the chamber;
releasing the tissue from the chamber; and
withdrawing the device.

In one embodiment the tissue is drawn into the chamber by applying a vacuum.

The tissue may be drawn towards the active element. The tissue may be drawn into contact with the active element.

In one embodiment the method comprises the step of applying a stimulus to the tissue using the active element.

In one case the method comprises the step of applying electrical energy to the tissue.

Alternatively or additionally the method comprises the step of applying electromagnetic energy to the tissue.

The method may comprise the step of applying nuclear energy to the tissue.

The method may comprise the step of applying heat energy via microwave or alternative energy source to the tissue.

In one case the active element comprises a conductive element. The active element may comprise an electrode and/or an optical element.

In one embodiment the active element comprises a radiation source.

The active element may comprise an ultrasound source.

In one embodiment the active element comprises all electrode and the treatment applied to the tissue is an electroporation treatment.

In one case the tissue is a diseased tissue such as a tumour. The tumour may be oesophageal, colon, bladder, stomach, kidney, liver, pancreatic, fibrosarcoma, breast, prostate, glioma, lung, rectal, spleen, ovary, or melanoma type.

Alternatively the tissue is a healthy tissue.

In one embodiment the method comprises the step of carrying out a further procedure on the tissue. The further procedure may be carried out before drawing tissue into the chamber. Alternatively or additionally the further procedure is carried out after drawing tissue into the chamber.

The further procedure may be a treatment procedure and/or a visualization procedure, and/or a drug treatment procedure, and/or a diagnostic procedure.

In one embodiment the method comprises the step of coupling one or more ancillary devices such as laparoscopic to the device.

The method may comprise the step of injecting a therapeutic agent into the tissue.

In one embodiment the device is mounted to or mountable to an instrument. The instrument may be an endoscope, laparoscope, thoracoscope, or ureteroscope. The instrument may comprise a catheter.

The device may be mounted to or mountable to a distal end of an instrument.

In one embodiment the method comprises the step of monitoring the treatment procedure using a sensor.

In another embodiment the method comprises the step of controlling the treatment procedure using a controller.

The site of interest may be a site on an external surface of a body. Alternatively the site of interest is an internal site within a body.

The device of the invention facilitates the endoscopic delivery of therapeutic agents to both normal and tumour tissue. The use of plate electrodes within the chamber allows for a homogenous electric field to be generated during the delivery of the electrical pulses. A defined volume of tissue is drawn within the chamber and safely held in place while the tissue is treated. This invention therefore allows for a defined volume of intraluminal tissue to be treated whether with electrical pulses or an alternative physical treatment that allows for the enhanced uptake of genetic or pharmaceutical agents. Since the discovery that electrical pulses could be used to safely enhance the uptake across the cell membrane of both genes and drugs, various electrode arrangements have been designed for use on both external and intraluminal tissue. Essentially the options have been limited to the use of either macro needle or plate electrodes. Clinically these electrodes have been applied to external tissue e.g. basal cell carcinoma and malignant melanoma, however due to the absence of suitable surgical tools for the application of electroporation to intraluminal tissue the technology has been unable to develop in this area. In the apparatus and method of the invention the volume of tissue being treated is treated to the optimal extent and as uniformly as possible. The effect of having the electrodes contained within a chamber is to allow the surgeon to have precise control of the tissue area being treated, in addition the risk of current leakage or damage to healthy tissue is minimised (as compared to the application with needle based electrodes) due to the electrodes being contained within the device chamber and the target tissue being held in place until the end of the procedure via the use of a vacuum suction.

Having the electrodes housed inside a tissue chamber allows tissue of known proportions (constraints imposed by the chamber size) to be drawn into that chamber. Once the tissue is in the chamber the tissue can be electrically tested via the electrodes or other incorporated sensors such as temperature sensors and with the resulting information the entrapped tissue can be evenly and efficiently electrically treated to provide the best effect or desired effect. This is possible due to the fixed known volume and characteristics such as electrode spacing within the chamber and size of the tissue chamber.

Entrapment of the target tissue within the chamber ensures that treatment is limited to that target tissue.

Drug treatment injected into the target tissue while the target tissue is held within the tissue chamber and hence between active devices such as electrodes ensures that the drug treated area is the electrically treated area.

Holding the target tissue within the chamber by reduced pressure during the injection of the treatment drug will aid the dispersal of that drug throughout the cellular free space prior to electrically treating the tissue. The cellular free space is the desired location of the treatment drug prior to electrically treating the target tissue.

The device of the invention can be provided on catheter, endoscope, laparoscope, thoracoscope, or ureteroscope to treat diseased, cancerous, tumourgenic and/or healthy human or animal tissue and/or organs.

The invention provides the application of vacuum pressure to help disperse any diagnostic, therapeutic, indicative, investigational solution within diseased, cancerous, tumourgenic and/or healthy human or animal tissue and/or organs. The vacuum suction may be applied through a manifold.

It will be appreciated that the volume of chamber can be altered at design/manufacture stage, to suit the application.

The device of the invention could be used for all known tumour types accessible both internally and extra-dermal, including but not limited to: oesophageal, colon, bladder, stomach, kidney, liver, pancreatic, fibrosarcoma, breast, prostate, glioma, lung, rectal, spleen, ovary, and melanoma.

The device facilitates delivery of drugs and/or gene therapies to target sites within the diseased, cancerous, tumourgenic and/or healthy human or animal tissue and/or organs. Thus the invention provides a minimally invasive device for the site specific delivery of both drugs and/or gene therapies to target sites within diseased, cancerous, tumourgenic and/or healthy human or animal tissue and/or organs.

The device may be used for the treatment of localised and defined volumes of diseased, cancerous, tumourgenic and/or healthy human or animal tissue and/or organ.

The invention provides an endoscope, laparoscope, thoracoscope, or ureteroscope catheter borne device designed specifically to deliver electrical pulses, nanoparticles, polymers, ultrasonic sound waves, microwaves, gene therapies, chemotherapies, and drugs.

The device may be used to deliver repeated follow up treatments via a minimally invasive protocol.

The device has conducting materials mounted in or on its walls and/or the chamber may be fitted with conducting materials. Such conducting materials allow for delivery of electrical pulses to diseased, cancerous, tumourgenic and/or healthy human or animal tissue and/or organs by employing the conducting material as electrodes.

In the case of metallic materials they can be any suitable biocompatible material, including but not limited to gold, platinum, and/or stainless steel.

The electrodes can be planar rigid electrodes, block electrodes, mesh electrodes, they may be manufactured by thin film deposition of metal on various substrates including but not limited to silicon, plastic, polymer, ceramic and the like.

The electrodes can be silicon or polymeric needle based electrodes of various dimensions, or arrays of same. Needles can be fabricated by machining. Needles or microneedles can be fabricated in silicon by Potassium Hydroxide (KOH) etching or by deep reactive ion etching (DRIE) etching. Needles or microneedles can be fabricated from polymers by methods including but not limited to polymer hot embossing.

The electrodes could be flexible electrodes and/or substances or substrates capable of conducting electrical pulses.

The chamber can include any number or arrangement or location of electrodes as required. Electrode arrangements can include any or all combinations of the above types of electrodes/conducting materials/conducting mechanisms.

The invention facilitates delivery of electrical pulses to diseased, cancerous, tumourgenic and/or healthy human or animal tissue and/or organs by employing electrodes or other conducting materials, as outlined above, capable of conducting/delivering nanoparticles, polymers, ultrasonic sound waves, microwaves, gene therapies, chemotherapies, and/or drugs. The invention also facilitates delivery of electrical pulses to diseased, cancerous, tumourgenic and/or healthy human or animal tissue and/or organs by employing electrodes or other conducting materials, as outlined above.

The device may be engineered to improve the delivery of gene and drug products and any diagnostic, therapeutic, indicative, investigational solution by enhancing their transport across the cell membrane.

The invention provides electroporation pulse delivery combined with localised delivery of a therapeutic agent via a septum or channel or port.

In one embodiment, the electrodes/conducting materials/mechanism on the device/chamber walls can accommodate such therapeutic agent delivery channels/routes. These delivery routes can be channels, microchannels, capillary channels, pores, holes, ports, needles, microfluidic channels, macrofluidic channels or the like.

A separate injection/microinjection needle which can extend into the chamber once (or before) the tissue/organ area being treated is in the chamber to facilitate injection of a therapeutic agent.

The device of the invention is capable of enhancing the delivery of genes and drugs and any diagnostic, therapeutic, indicative, investigational solution across the cell membrane via a minimally invasive procedure using either endoscopic, laparoscopic, thoracoscopic, or ureterscopic catheter borne devices.

The device may be used to assist in the down-staging of tumour volume prior to surgery or other treatment. More particularly, the device may be used to assist in the down-staging of tumour volume before surgery or other treatment by delivering electrical pulses via an endoscope, laparoscope, thoracoscope, or ureteroscope catheter combined with injecting a drug or any diagnostic, therapeutic, indicative, investigational solution to the tumour tissue.

The device may be used to assist in the down-staging of tumour volume before surgery or other treatment by delivering nanoparticles, polymers, ultrasonic sound waves, microwaves, gene therapies, chemotherapies, and drugs via an endoscope, laparoscope, thoracoscope, or ureteroscope catheter combined with injecting a drug or any diagnostic, therapeutic, indicative, investigational solution to the tumour tissue.

Any suitable down-staging technique may be used including heat/delivery of other forms of radiation/energy and the like.

The invention facilitates delivery of a homogenous electrical field to diseased, cancerous, tumourgenic and/or healthy human or animal tissue and/or organs via laparoscopic or endoscopic means.

The invention provides an endoscopic, laparoscopic, thoracoscopic, ureterscopic based device capable of injecting a gene or drug solution or any diagnostic, therapeutic, indicative, investigational solution at specific diseased, cancerous, tumourgenic and/or healthy human or animal tissue and/or organs, and simultaneously providing a real time visual output for monitoring of the procedure.

The invention also provides an endoscopic, laparoscopic device capable of injecting a gene or drug solution or any diagnostic, therapeutic, indicative, investigational solution at specific diseased, cancerous, tumourgenic and/or healthy human or animal tissue and/or organs, delivering electrical pulses site specifically to fixed volumes and simultaneously providing a real time visual output for monitoring of the procedure.

The invention further provides an endoscopic, laparoscopic device capable of injecting a gene or drug solution or any diagnostic, therapeutic, indicative, investigational solution at specific diseased, cancerous, tumourgenic and/or healthy human or animal tissue and/or organs, delivering electrical pulses specifically to fixed tissue volumes of diseased, cancerous, tumourgenic and/or healthy human or animal tissue and/or organs and simultaneously providing a real time visual output for monitoring of the procedure, in addition to monitoring of any temperature, pH, permeability, impedance, conductivity changes that may occur during the procedure.

The device facilitates delivery of electrical pulses to induce a stress response in diseased, cancerous, tumourgenic and/or healthy human or animal tissue and/or organs.

The invention enables delivery of defined electrical pulses to diseased, cancerous, tumourgenic and/or healthy human or animal tissue and/or organs causing a loss of cell function in response to environmental stresses, including but not limited to temperature, pH, permeability, impedance, conductivity.

The invention also enables delivery of defined electrical pulses to diseased, cancerous, tumourgenic and/or healthy human or animal tissue and/or organs causing a disruption across the cell nucleus and altering the ability of the cell to respond to environmental stresses.

The invention provides a device to draw diseased, cancerous, tumourgenic and/or healthy human or animal tissue and/or organs within a chamber under vacuum pressure, with the additional characteristics or capabilities of allowing injection of a genetic or drug solution or any diagnostic, therapeutic, indicative, investigational solution specifically to the diseased, cancerous, tumourgenic and/or healthy human or animal tissue and/or organs and for subsequent delivery of electrical pulses to the diseased, cancerous, tumourgenic and/or healthy human or animal tissue and/or organs via conductive electrodes spaced apart on either inner wall of the chamber. Furthermore, the electrodes have been designed to incorporate temperature chips to allow for real time monitoring of the tissue temperature before, during and after delivery of electrical pulses, while the chamber also allows for monitoring via a visual output device. The device may also have the capacity to be altered to allow for its attachment or integration to an endoscope or laparoscope or other suitably engineered device to allow for application of the device to diseased, cancerous, tumourgenic and/or healthy human or animal tissue and/or organs employing as minimally invasive a procedure as possible. The device may be integrated onto a laparoscope, thoracoscope, ureteroscope or endoscope. The device can also be engineered to allow for the delivery of ultrasonic energy to diseased, cancerous, tumourgenic and/or healthy human or animal tissue and/or organs. The device can also be engineered to allow for the delivery of microwave energy to diseased, cancerous, tumourgenic and/or healthy human or animal tissue and/or organs.

In addition the device may be used to deliver nanoparticles site specifically to diseased, cancerous, tumourgenic and/or healthy human or animal tissue and/or organs. More particularly, the device may be used to deliver nanoparticles site specifically to diseased, cancerous, tumourgenic and/or healthy human or animal tissue and/or organs and for subsequent delivery of electrical pulses to diseased, cancerous, tumourgenic and/or healthy human or animal tissue and/or organs via conductive electrodes spaced apart on either inner wall of the chamber.

The invention enables application of electrical pulses, ultrasound and microwave energy to diseased, cancerous, tumourgenic and/or healthy human or animal tissue and/or organs.

The invention also enables application of electrical pulses and ultrasound to diseased, cancerous, tumourgenic and/or healthy human or animal tissue and/or organs to reduce tumour volume.

Electrical pulses and microwave energy may be applied to diseased, cancerous, tumourgenic and/or healthy human or animal tissue and/or organs to reduce tumour volume via sensitising the cells to heat after electroporation.

In one aspect the invention provides a device to draw diseased, cancerous, tumourgenic and/or healthy human or animal tissue and/or organs within a chamber under vacuum pressure, with the additional characteristics or capabilities of allowing injection of a genetic or drug solution or any diagnostic, therapeutic, indicative, investigational solution specifically to diseased, cancerous, tumourgenic and/or healthy human or animal tissue and/or organs and for subsequent delivery of electrical pulses to diseased, cancerous, tumourgenic and/or healthy human or animal tissue and/or organs via conductive electrodes spaced apart on either inner wall of the chamber. Furthermore the device is capable of delivering microwave energy to electric pulse-sensitised diseased, cancerous, tumourgenic and/or healthy human or animal tissue and/or organs within the chamber.

In another aspect the invention provides a device to draw diseased, cancerous, tumourgenic and/or healthy human or animal tissue and/or organs within a chamber under vacuum pressure, with the additional characteristics or capabilities of allowing injection of a genetic or drug solution or any diagnostic, therapeutic, indicative, investigational solution specifically to diseased, cancerous, tumourgenic and/or healthy human or animal tissue and/or organs and for subsequent delivery of nanoparticles, polymers, ultrasonic sound waves, microwaves, gene therapies, chemotherapies, and drugs to diseased, cancerous, tumourgenic and/or healthy human or animal tissue and/or organs via conductive electrodes spaced apart on either inner wall of the chamber. Furthermore the device is capable of delivering microwave energy to electric pulse sensitised diseased, cancerous, tumourgenic and/or healthy human or animal tissue and/or organs within the chamber.

The invention also provides a device to draw diseased, cancerous, tumourgenic and/or healthy human or animal tissue and/or organs within a chamber under vacuum pressure, with the additional characteristics or capabilities of allowing injection of a genetic or drug solution or any diagnostic, therapeutic, indicative, investigational solution specifically to diseased, cancerous, tumourgenic and/or healthy human or animal tissue and/or organs and for subsequent delivery of nanoparticles, polymers, ultrasonic sound waves, microwaves, gene therapies, chemotherapies, and drugs to diseased, cancerous, tumourgenic and/or healthy human or animal tissue and/or organs via conductive electrodes spaced apart on either inner wall of the chamber.

Furthermore the device is capable of delivering nanoparticles, polymers, ultrasonic sound waves, microwaves, gene therapies, chemotherapies, and drugs to diseased, cancerous, tumourgenic and/or healthy human or animal tissue and/or organs sensitised to nanoparticles, polymers, ultrasonic sound waves, microwaves, gene therapies, chemotherapies, and drugs within the chamber.

A device can draw diseased, cancerous, tumourgenic and/or healthy human or animal tissue and/or organs within a chamber under vacuum pressure and may contain micro needles, typically of silicon, that assist in maintaining the tissue within the chamber.

This invention relates to physical treatment of tumours and tissue. In particular, this invention is concerned with the treatment of tumour or otherwise diseased tissue in a region that is localised and of defined volume. The tissue is brought into proximity with the means of treatment typically by implementing the invention as a treatment head in the form of an attachment to a medical device, typically an endoscope or a laparoscope. An important aspect of the invention concerns the enhancement of the efficacy of a therapeutic agent by the application of a physical stimulus and the optimisation of the uniformity of the physical field experienced by the treated volume. A further aspect of the invention is that it can be implemented as a disposable treatment head for use on an individual patient in a single treatment session.

In this invention in order to improve the uniformity of the impressed physical field, the treatment volume is regularly defined by the chamber and is imposed upon the otherwise irregularly shaped tissue to be treated by drawing the tissue into the chamber. This has been found to be preferable to a less regularly shaped volume. Through the use of an endoscope visual information allows for relatively precise positioning of the means of treatment. Surprisingly, in this invention, we have found that the improved definition of the treatment volume can be achieved by using vacuum or suction to draw the tissue to be treated into an appropriately shaped cavity with an optimum array of active elements for the process enhancements involved.

The use of negative pressure in this way has the added benefit of reducing interstitial pressure than can be elevated in tumour tissue, such a reduction improving the uptake by the tissue of therapeutic agent. The therapeutic agent can be delivered by injection, from an intravenous drip or it can be injected into the volume of tissue after it has been drawn into the treatment head.

In the case where the volume of tumour or tissue to be treated is large relative to the volume treated on each occasion, adjacent volumes of diseased tissue can be treated by indexing the treatment volume over the diseased volume. The visualisation provided by the endoscope allows this to be achieved relatively precisely. Furthermore the processes involved generate physical changes such as increase in temperature, and it is useful to follow the processes using appropriate sensing means, such as a temperature sensor.

BRIEF DESCRIPTION OF THE DRAWINGS

The invention will be more clearly understood from the following description of some embodiments thereof, given by way of example only, with reference to the accompanying drawings, in which:—

FIG. 2 is a side view of the apparatus of FIG. 1;

FIG. 3 is an end view of the apparatus of FIG. 1;

FIG. 4 is a perspective view of the component parts of the apparatus of FIG. 1;

FIG. 5 is a perspective view of the component parts of FIG. 4 assembled to form the apparatus of FIG. 1;

FIG. 7 shows suction ports but not active elements, while in FIG. 8 both suction ports and active elements are omitted for clarity;

FIG. 17 is a diagram of an endoscope with the device of the invention.

DETAILED DESCRIPTION

Figure 1:
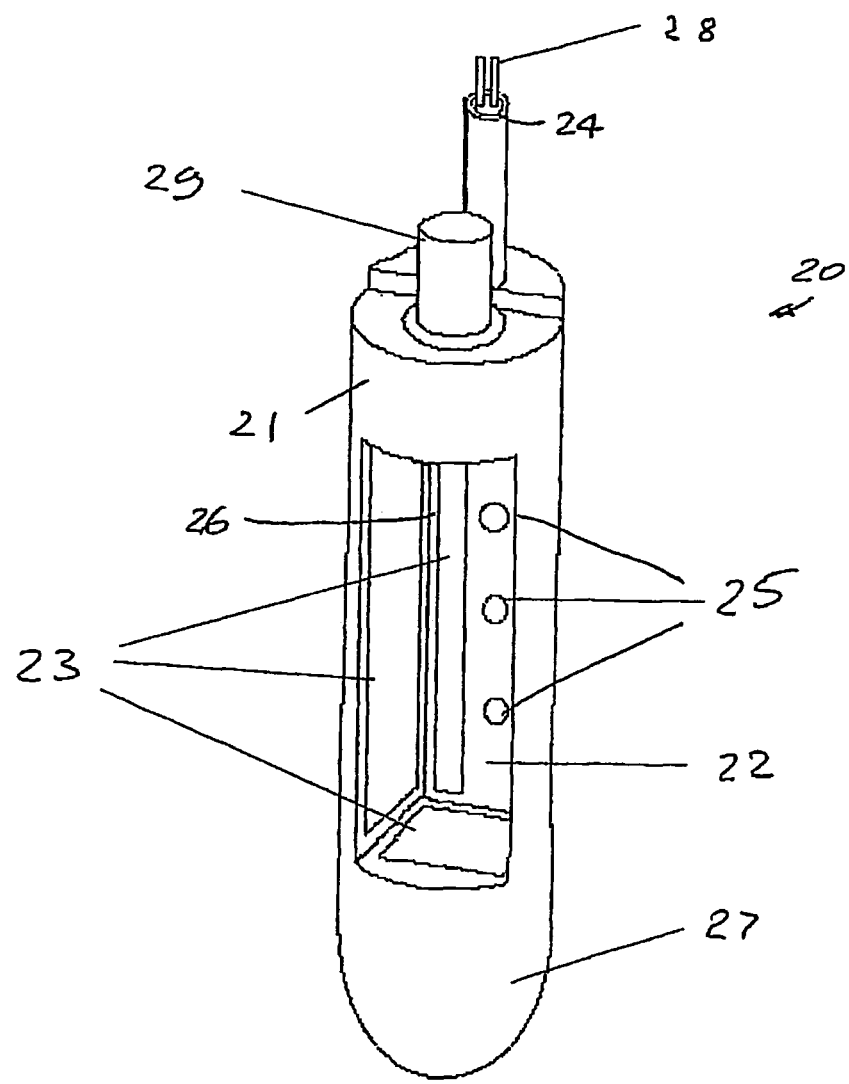
FIG. 1 is a perspective view of an apparatus for carrying out a prophylactic or treatment procedure on tissue according to the invention.

Referring to the drawings, and initially to FIGS. 1 to 5 thereof, there is illustrated an apparatus 20 according to the invention. The apparatus 20 is suitable for carrying out a prophylactic or treatment procedure on tissue.

The apparatus 20 comprises a device 21 having a treatment chamber 22 and a plurality of active elements 23 within the chamber 22, and a vacuum lumen 24.

The chamber 22 has a large opening 26 at a side of the chamber 22, through which tissue can be drawn into the chamber 22.

The proximal end of the vacuum lumen 24 is connected in communication with a vacuum source located externally of a body, and a distal end of the vacuum lumen 24 is connected in communication with the chamber 22 by means of a plurality of vacuum orifices 25 in the rear wall of the chamber 22.

The vacuum lumen 24 may be employed to apply a vacuum to tissue, and in this way to draw tissue into the chamber 22 into contact with the active elements 23.

As illustrated in FIG. 3, the longitudinal axis A-A of the vacuum lumen 24 is offset radially from the longitudinal axis B-B of the chamber 22.

In this case each active element 23 is provided in the form of a rigid planar member fixedly attached to the interior wall of the chamber 22. Each active element 23 comprises an electrode for applying an electroporation treatment to tissue drawn into the chamber 22, and an integral sensor for monitoring the treatment procedure.

The location of the active elements 23 within the chamber 22 is chosen to minimise the variation in intensity of the electric field within the chamber 22. In this manner, the device 21 achieves a substantially homogenous physical field throughout the chamber 22.

Connecting leads 28 connect the active elements 23 in communication with a controller located externally of a body. To minimise the overall volume of the apparatus 20, the connecting leads 28 extend through the vacuum lumen 24, which acts as a housing around the connecting leads 28.

The device 21 has a port 29 to facilitate coupling of one or more ancillary laparoscopic devices to the device 21. As illustrated in FIG. 3, the port 29 is aligned with the chamber 22 so that the ancillary laparoscopic device will be coupled to the device 21 aligned with the chamber 22.

Suitable ancillary laparoscopic devices that may be coupled to the device 21 include an endoscope for transmitting visual information in relation to the prophylactic or treatment procedure being performed on tissue, and/or a needle for injecting a therapeutic agent into tissue drawn into the chamber 22.

As illustrated in FIGS. 2 and 3, the distal end 27 of the device 21 is substantially rounded. In this way the device 21 defines a smooth crossing profile. The device 21 is formed of a moulded body, in this case.

The apparatus 20 may be mounted to an instrument for delivery to a site of interest in a body and subsequent retrieval from the body. Typically the apparatus 20 will be mounted to the distal end of the instrument.

Suitable instruments to which the apparatus 20 may be mounted include an endoscope, a laparoscope, a thoracoscope, a ureteroscope, a catheter.

In use, the apparatus 20 is mounted to an instrument, and the instrument is advanced through a body to deliver the apparatus 20 to a desired site of interest within the body. A vacuum is then applied using the vacuum source externally of the body. The vacuum is exerted on tissue via the vacuum lumen 24 and the vacuum orifices 25 to draw the tissue into the chamber 22 and into contact with the active elements 23.

The electrodes in the active elements 23 are used to apply an electroporation treatment to the tissue in the chamber 22. During the treatment procedure, the sensors in the active elements 23 enable the user to monitor the progress of the treatment procedure, and the progress of the treatment procedure may be controlled using the controller.

When the treatment procedure has finished, the vacuum is released to release the tissue from within the chamber 22, and the apparatus 20 is retrieved from the body by withdrawing the instrument.

A further procedure may be carried out on the tissue before and/or after drawing tissue into the chamber 22. Possible further procedures include a treatment procedure, a visualisation procedure, a drug treatment procedure, or a diagnostic procedure.

The apparatus 20 of the invention is suitable for treating a diseased tissue, such as a tumour. The tumour may be oesophageal, colon, bladder, stomach, kidney, liver, pancreatic, fibrosarcoma, breast, prostate, glioma, lung, rectal, spleen, ovary or melanoma type.

The apparatus 20 of the invention is also suitable for carrying out a prophylactic treatment on healthy tissue.

The site of interest may be an internal site within the body, or an external site on an external surface of the body.

It will be appreciated that the configuration of the device 21 may be altered to suit the requirements of the clinical procedure and/or to suit the requirements of the anatomy of the patient. For example the opening to the chamber may alternatively or additionally be provided at an end of the chamber 22. The chamber may have a plurality of openings.

It will also be appreciated that the active elements may be provided in a variety of possible forms. For example the active element may comprise a conductive element, and/or an optical element, and/or a radiation source, and/or an ultrasound source. The active element may apply a physical stimulus, and/or electrical energy, and/or electromagnetic energy, and/or nuclear energy, and/or heat energy to the tissue. The active element may be impregnated with a therapeutic agent.

Each active element within the chamber 22 may be the same. Alternatively two or more of the active elements within the chamber 22 may differ from one another.

Figure 6:
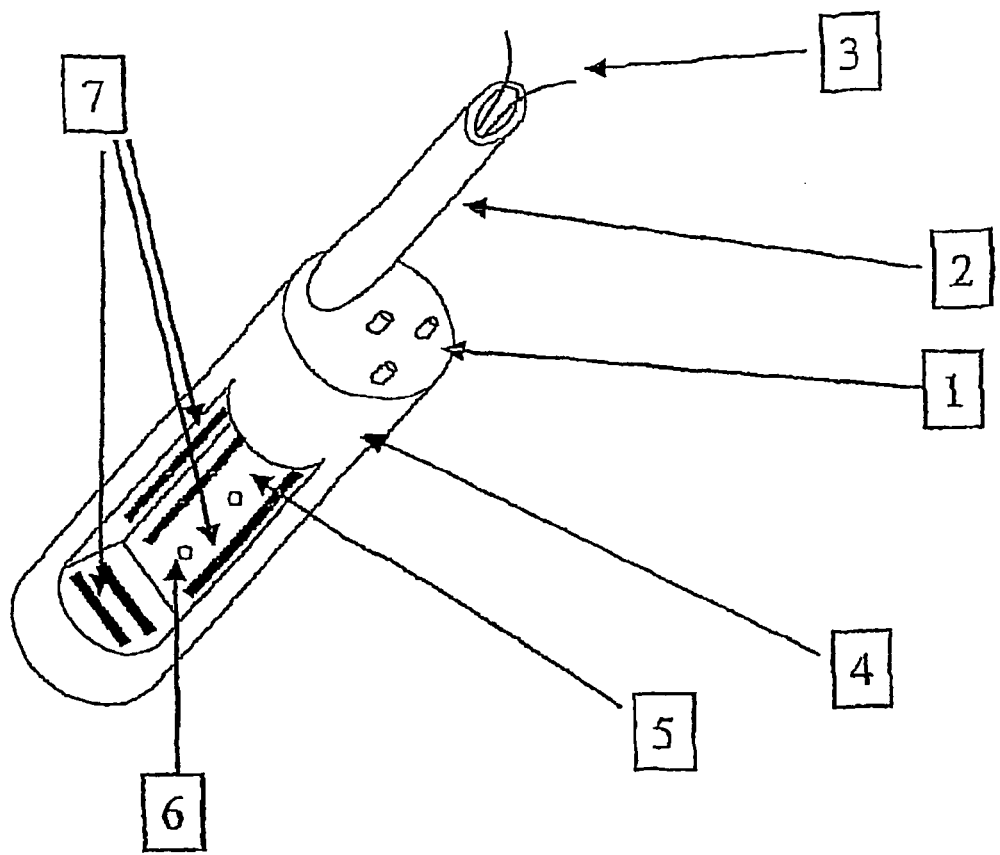
FIG. 6 shows a general view of one embodiment of the invention.

In FIG. 6 there is illustrated another apparatus according to the invention, which is similar to the apparatus 20 of FIGS. 1 to 5.

FIG. 6 shows a body 4 that is moulded or machined and made from biocompatible metal, polymer or ceramic material that is approved for short-term use in the human body. Within the body there is formed a chamber 5, the internal walls of which define a regular cross section into which tissue or tumour is drawn by the application of a vacuum to the chamber 5 via the lumen 2 and multiple orifices 6 connected to the lumen 2 via the internal manifold 8. The vacuum is generated by a suction pump or other means connected to the proximal end of the lumen 2. In the walls of the chamber 5 there are located active element means 7 for impressing onto the tissue drawn into the chamber 5 the physical stimulus, the active elements 7 being arranged in such a way as to minimise the variation in intensity of the physical field within the chamber 5. Integral within or separate from the active element means 7 are optional sensors for monitoring the progress of the treatment process also located in the walls of the chamber 5. Typically sensors and active elements 7 will be connected to external circuits via connecting wires and/or optical fibres that are conveniently but not necessarily located within the vacuum lumen 2. Where contacting means 7 is employed for the application of an electric field, or other electrical processes, such as RF heating for example, the active elements 7 can be planar, interdigitated or otherwise shaped and can incorporate features appropriate to the scale of the process or processes being employed for enhancement purpose. Sources of ultrasound can also be active elements. Where therapy stimulated by radiation in or adjacent to the visible spectrum is employed contacting means 7 can be tailored precisely by the use of both refractive and reflective rigid elements so as to achieve the required intensity distribution in the treatment volume.

The end face of moulded body 4 contains, in addition to the means for attaching lumen 2 mechanical features 1 for registering it with the end face of an endoscopic device 12 so as to form a rigid extension that does not obscure the means integral within the body of the endoscope for transmitting visual information to the proximal end so that the surgeon can observe the processes being carried out at the distal end. In an alternative configuration, the vacuum tube attached to the device is taped to the outside of the body of the endoscope. Any electrical conductors and/or optical fibres that are required, and located for convenience inside the vacuum tube can be separated at the control end of the endoscope leaving one port for the vacuum and others for the electrical and/or optical connections.

Figure 7:
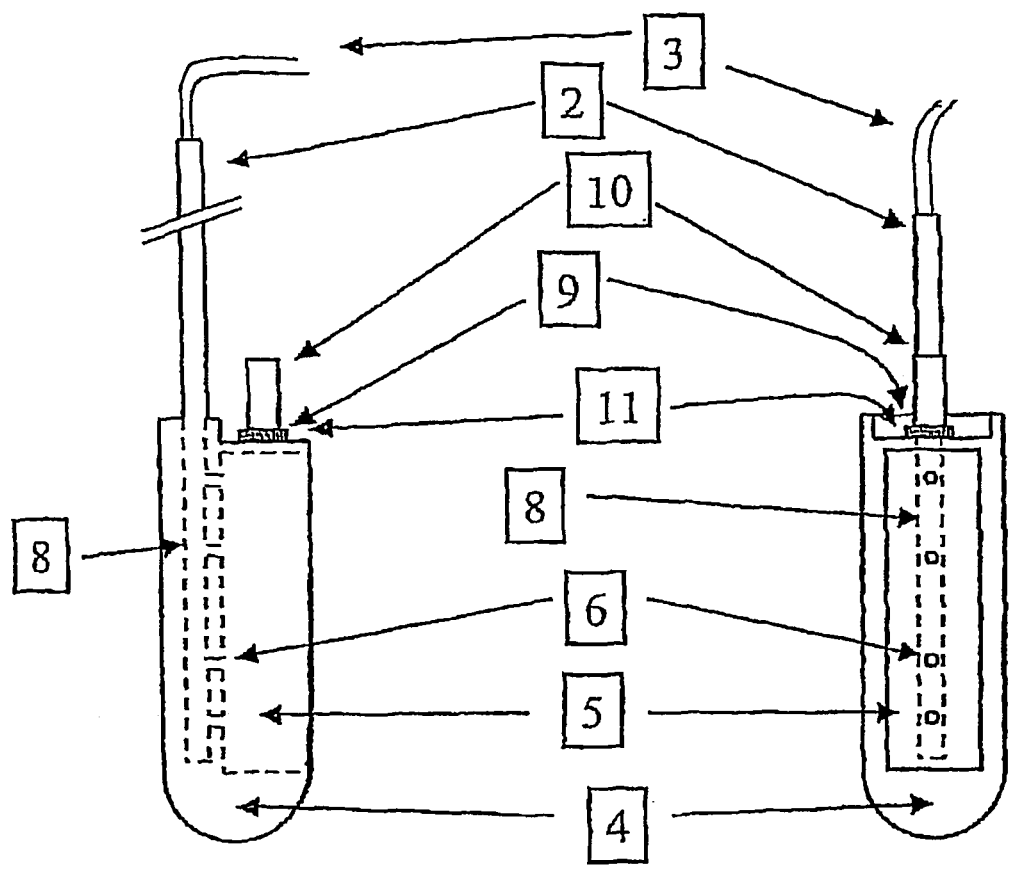
FIG. 7 illustrates details of the construction of the device by showing orthogonal vertical sections.
Figure 8:
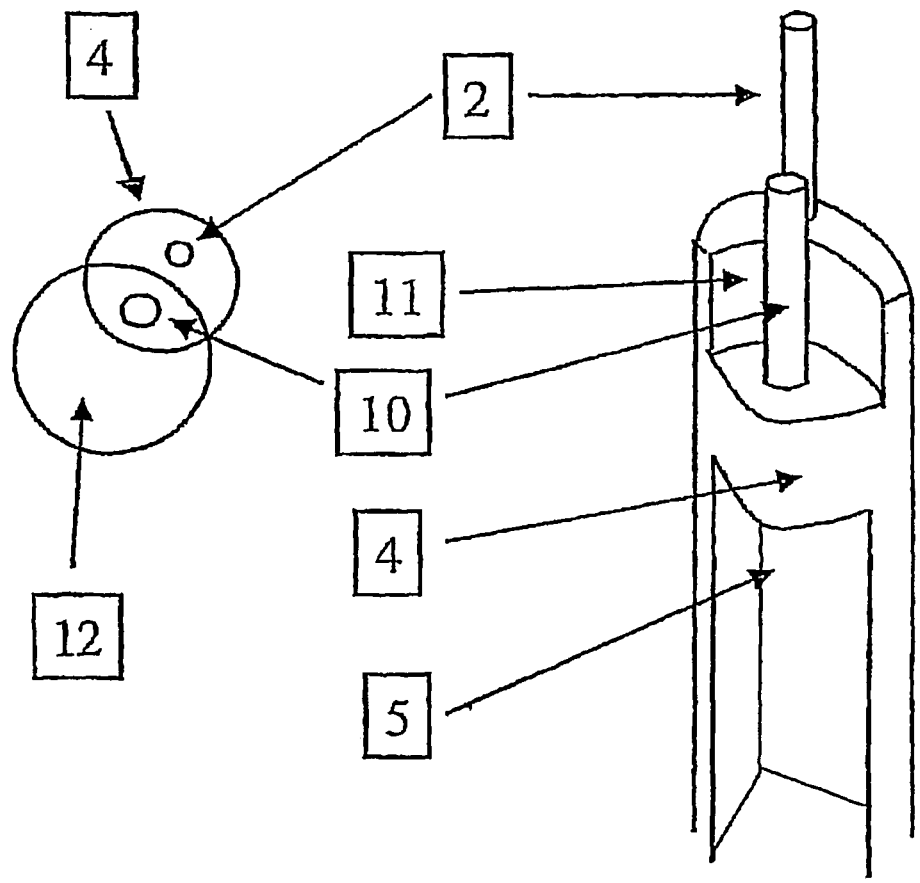
FIG. 8 illustrates one means of attaching an embodiment to the end of an endoscope.

FIGS. 7 and 8 show another embodiment of the invention, in which the mechanical features 1 comprise a hollow peg 10 that fits into the biopsy port of the endoscopic means, and a 'half moon' step 11 machined out of the body 4 of radius similar to that of the body of the endoscopic means, such that when the peg 10 is located within the biopsy port of the endoscope, the body 2 is unable to rotate relative to the endoscopic body 12, and is thus rigidly fixed in the rotational axis about the peg. Between the body 4 and the peg 10 there can be located a septum that acts to seal the internal parts of the endoscopic means from the applied vacuum, and through which a needle can be inserted via the biopsy channel to act as a further means for contacting the tumour or tissue, and through which a therapeutic agent can be injected into the tumour or tissue. In this case the mild vacuum creates a negative pressure drawing the therapeutic agent into and around the contained surface of the tissue or tumour. In this embodiment the vacuum tube is taped to the outside of the endoscope.

Figure 9:
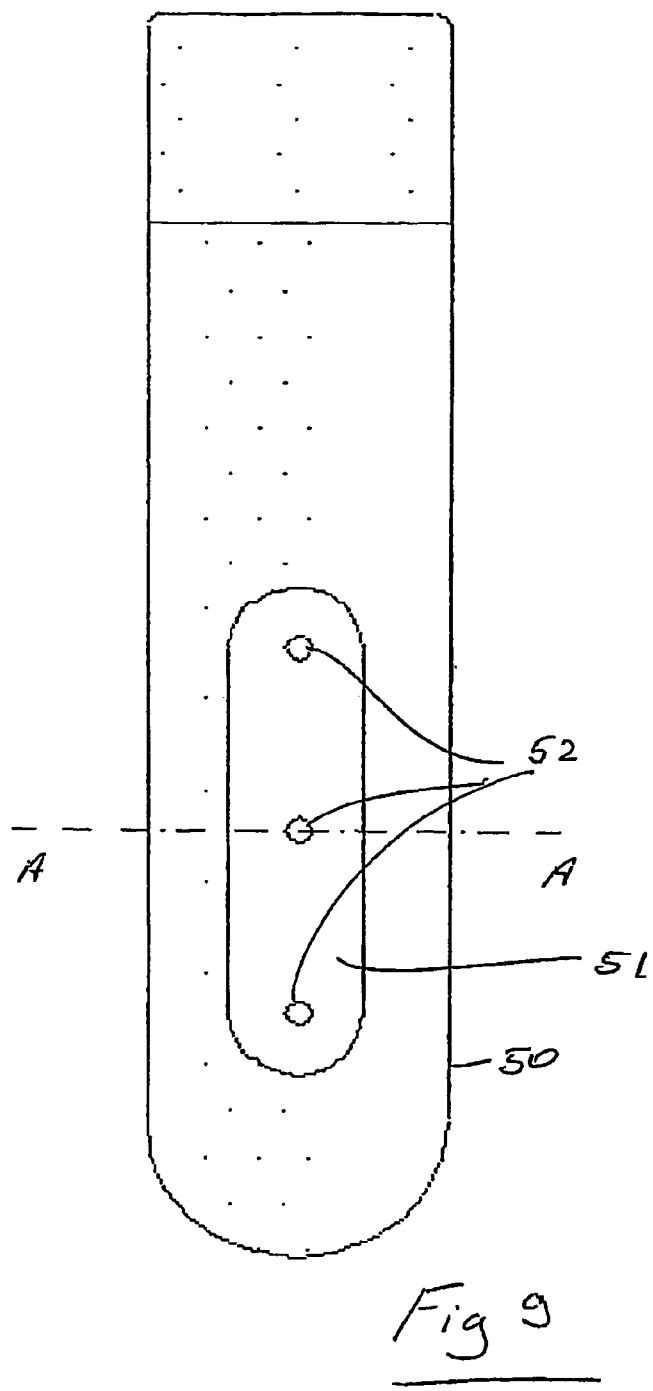
FIG. 9 is an elevational view of another device of the invention.
Figure 10:
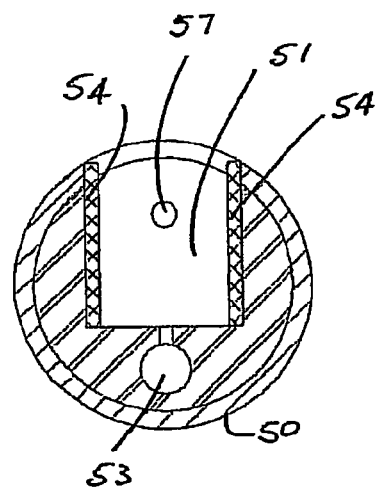
FIG. 10 is a cross-sectional view on the line A-A in FIG. 9.

Referring to FIG. 9 and FIG. 10 there is illustrated a simplified version of the device of the invention comprising a housing 50 having a tissue receiving chamber 51 with vents 52 leading from the chamber 51 to an underlying reduced pressure manifold 53. Electrodes 54 are in this case positioned in the side walls of the chamber 51. The device also has an injection port 10.

Figure 11A:
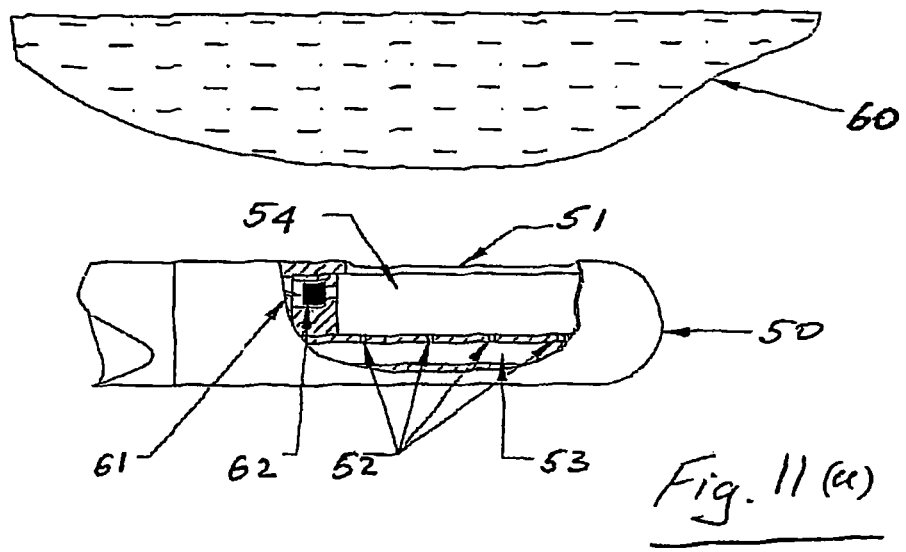
FIGS. 11(a) to 11(c) are diagrams illustrating a method of using the apparatus of the invention.
Figure 11B:
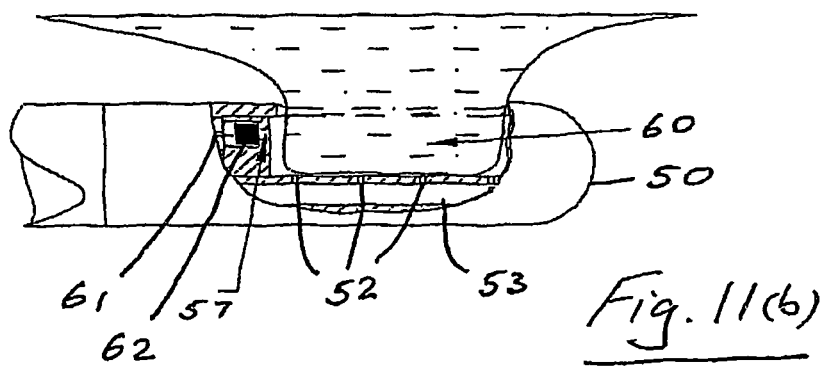
Figure 11C:
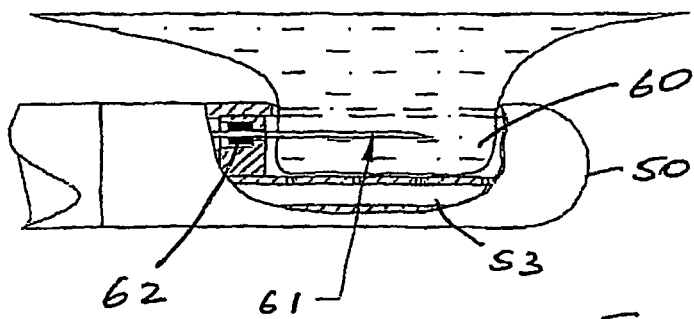

One use of the devices of the invention is illustrated in FIGS. 11(a) to 11(c). In this case target tissue is indicated by reference 60 and a treatment needle 61 which is passed through an injection septum or valve 62 is also illustrated. As illustrated in FIG. 11(a) the treatment head tissue chamber 51 is offered up to the target tissue 60. The treatment head 50 is cut-away to show the chamber 51, electrode 54, reduced pressure manifold 53 with tissue chamber vents 52 and injection septum 62. FIG. 11(b) illustrates visualisation of the entrapped target tissue 60 after the activation of the vacuum system when the treatment head 50 is applied to the surface of the target tissue 60. While the target tissue 60 is held by the reduced pressure within the tissue chamber 51, the treatment needle 61 (such as for a delivery of a drug) is pushed through the injection septum 62 and into the entrapped tissue 60 [FIG. 11(c)]. The treatment (such as a drug treatment) is applied into the target tissue while the tissue is held under reduced pressure prior to applying the treatment pulse.

Figure 12:
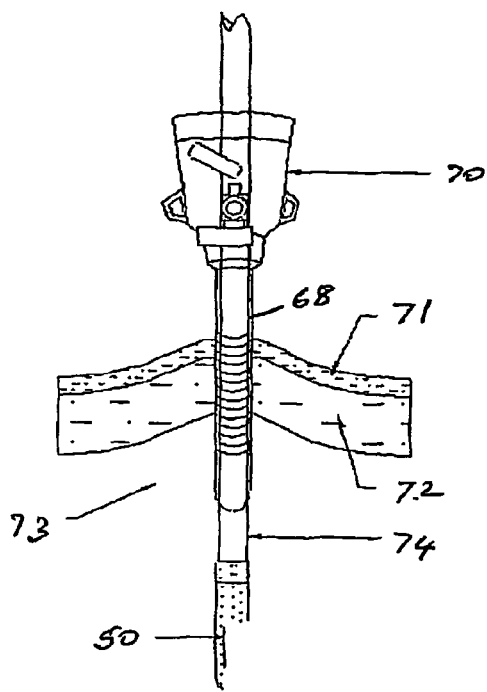
FIG. 12 is a cross-sectional view of a typical laparoscopic port with the device of the invention in place.
Figure 13:
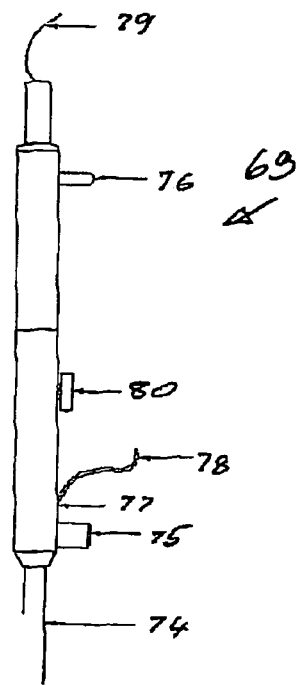
FIG. 13 is a view of a proximal handle end of the access port.

FIG. 12 illustrates a typical laparoscopic port 70 for use in the invention. The port 70 comprises a cannula 68 which is inserted through the epidermis 71 and subcutaneous tissues 72 into a body cavity 73. The treatment head 50 is attached to a laparoscopic shaft 24 and the shaft is passed through the port 70 and the cannula 68 into the body cavity 23 to gain access to the internal tissues/organs. A reduced pressure line 78, low dead volume treatment delivery tubing 79 and the electrical input/output wiring pass up through the inside of the shaft 74 to a proximal handle section 69. The proximal handle arrangement 69 is illustrated in FIG. 13. An electrical input/output connector 75 allows connection of the treatment head to a signal generator/analyser. A reduced pressure line 78 emerges from the handle 69 at a port 79 and may then be attached to a vacuum pump. A low dead volume treatment (e.g. drug) delivery tube 79 in this case passes the fill length of the handle 64 and emerges at the upper end and may then be attached to a pressurised injection device. The handle arrangement 69 has a thumb operated activator 76 for the injection system and a handle swivel lock nut 80.

Figure 14A:
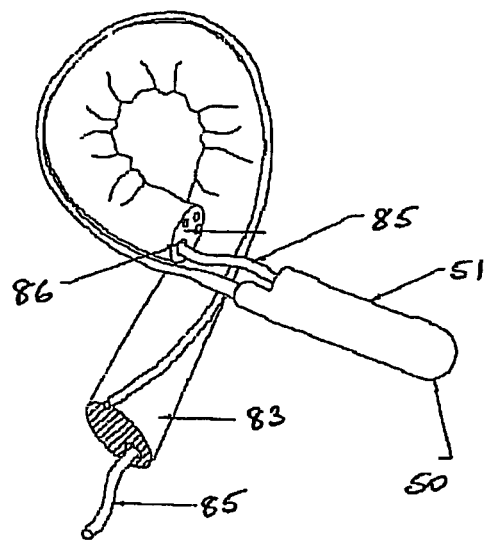
FIGS. 14(a) and 14(b) are perspective views of the device of the invention mounted to the end of a laparoscope.
Figure 14B:
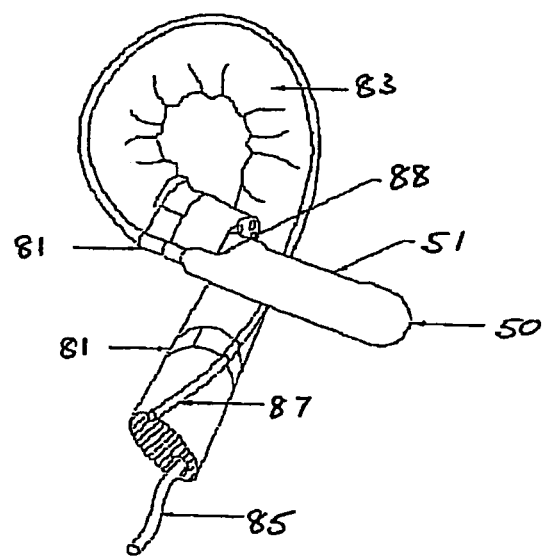
Figure 15:
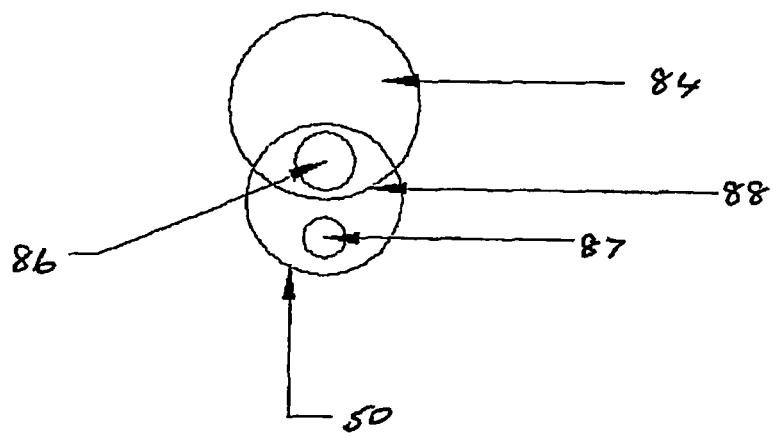
FIG. 15 is a cross-sectional view of a detail of FIG. 14 illustrating the mounting of the device to the endoscope.

A treatment head 50 of the invention attached to a typical endoscope is illustrated in FIGS. 14(a) and 14(b). The treatment head 50 is in a form for attachment to an endoscope distal end 84. An injection guide tube 85 from the treatment head 50 is passed up through a biopsy port 86 of the endoscope 83. When the treatment head 50 is seated against the endoscope end 84 using a half moon cut-out 88 on top of the treatment head 50, surgical tape 81 may be used to secure the reduced pressure line 87 to the outside of the endoscope 83. The reduced pressure line 87 also houses the electrical input/output wires from the treatment head 50. Referring especially to FIG. 15 the half moon shaped cut-out 88, once seated against the endoscope distal end 84 prevents the treatment head 50 from swivelling due to the offset positioning of the endoscope biopsy port 86.

Figure 16:
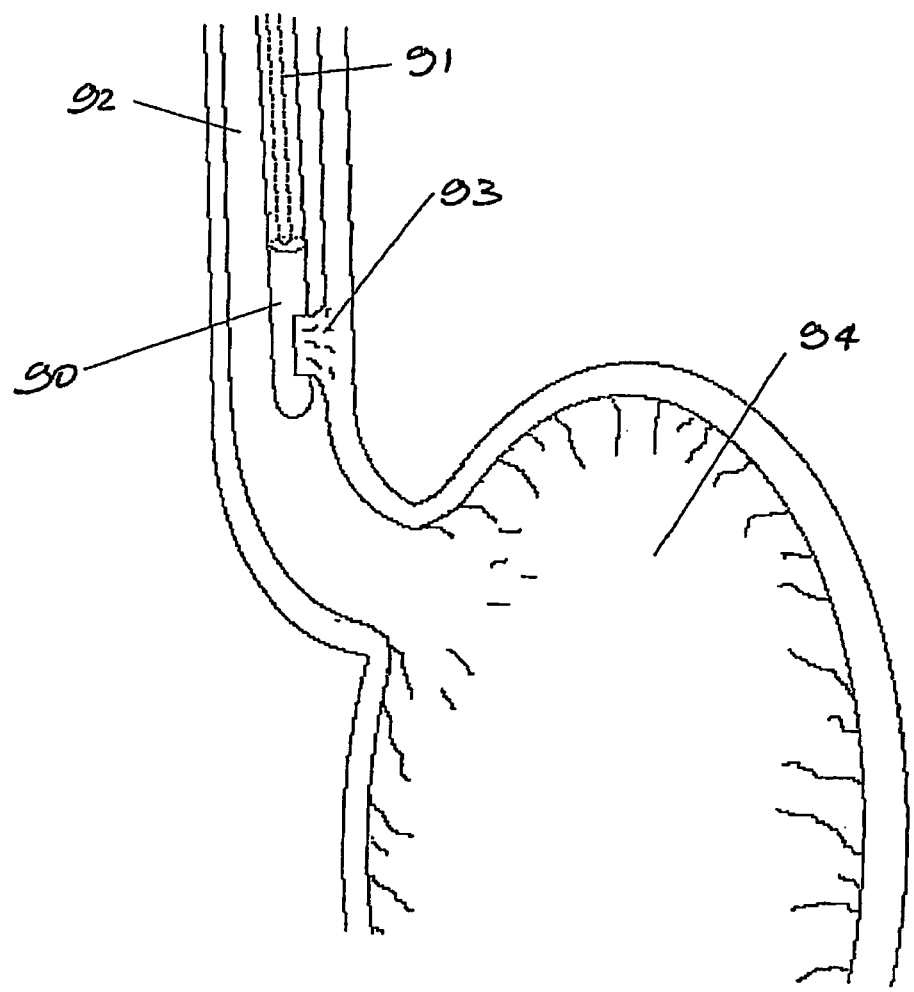
FIG. 16 is a diagram illustrating the application of the device of the invention to intraluminal oesophageal tissue via an endoscope.

Referring to FIG. 16 there is illustrated another application of the invention to intraluminal oesophageal tissue. A treatment head 90 of the invention is provided at a distal end of an instrument (such as an endoscope) shaft 91 and inserted into a squamous oesophagus 92 to access a tumour 93 which in this case is near the stomach 94. A treatment procedure or a number of such procedures as described herein may be applied to the tumour, when it has been drawn into the treatment chamber.

FIG. 17 illustrates the integration of a treatment head 95 of the invention onto the distal end 96 of an endoscope 97. The endoscope 97 has a proximal end with an eyepiece 98 and various ports 99 for wires, instruments and the like. A side section has a flexible shaft 100 for transmission of light, air, water and the like. Typically, a main shaft 10 of the endoscope is flexible.

The invention is further described by way of the following examples.

One embodiment of the invention is formed from machined nylon in three parts. The cap and body form a hollow cylinder 11 mm in diameter and 35 mm long with a hemispherical shape at the distal end. In the wall of the cylinder the opening for drawing in tissue into the chamber is formed. The cap includes the tubes and other features to connect to the endoscope and for transmitting the physical stimulus to the active elements. The active elements and vacuum connection to the chamber are fabricated as a separate sub-assembly that allows in this case metallic electrodes to be attached to the inner walls of the insert prior to sealing in place within the case and to the top. The volume of the chamber is 5×5×15 (all dimensions in mm).

In a second embodiment a two-part construction is employed. The case and top are formed from one piece of acetyl plastic while the insert and end cap are formed from another piece of acetyl plastic. This arrangement gives a more robust device that is unlikely to separate during use while still allowing initial access to the insert for fitment of the active elements.

In both embodiments the alignment of the device is offset from the end of the endoscope and the curve described by the endoscope periphery is cut into the top of the cap to a depth 5 mm. In conjunction with a 4.2 mm tube that locates into the biopsy port of the endoscope this locks the body in position and prevents rotation during use.

In one embodiment the vacuum line is made from 4.5 mm OD silicon rubber tubing that also acts as the conduit for the connecting wires and is taped to the outside of the endoscope before insertion into a patient. Alternatively 1.9 mm OD polyurethane catheter tubing is used which is less intrusive. Kevlar filaments can be included within the vacuum tube as well as cables or optical fibres so as to minimise damage through stretching. A suitable electrical conductor used for some devices is 0.91 mm OD coaxial wire (Nexans Filotex). The coaxial wire is first soldered to the edge of the active elements using standard LMP solder prior to being secured to the walls of the chamber.

The vacuum line is secured to a stainless steel tube that is fixed into a 1.2 mm hole that runs the length of the acetyl insert. Two or three openings to the vacuum are created in the back wall of the chamber to draw in the tissue. For example 0.3 mm holes are drilled through the chamber floor into the 1.2 mm diameter conduit. In tests a negative pressure of 0.6 atmospheres is needed to draw tissue into and fill the chamber. The vacuum holes can be profiled so as to minimise the possibility of becoming blocked by tissue if repeat applications are employed on a large volume of tissue or tumour.

Stainless steel electrodes are fixed into the walls of the chamber using 301 EpoTek medical adhesive. This adhesive readily adheres to the electrodes but is less good for bonding acetyl plastic. To overcome this a glue rivet method is employed where 1 mm countersunk holes are first drilled through the side-walls of the insert. The electrodes are then held in position and 301 medical adhesive applied until the holes become filled. Once the 301 has cured overnight at room temperature, the taper wedge created holds the electrodes firmly in place. The insert with electrodes is fitted into the outer case and bonded using 301 medical adhesive, the device sealed and the chamber floor coated with Dow Corning 731 silicon rubber. The unit is finished by addition of the vacuum line and an electrical connector. This design and the method of fabrication is quite flexible, allowing for example variations in the electrode spacing or orifice size.

Alternative methods of manufacturing the treatment chamber include injection moulded as a single piece using a multi-part tool with inserts to incorporate the means of contacting the treatment volume. This method of manufacture would be particularly suited to the implementation as a disposable treatment head for use on an individual patient in a single treatment session.

Units with the following dimensions have been made with multiple electrodes arranged evenly down the side-walls of the chamber and suitable for the application of an electric field to the tissue volume.

a. 10 mm long opening, 5 mm wide (electrode to electrode) and 5 mm deep;
b. 10 mm long opening, 4 mm wide gap and 5 mm deep;
c. 10 mm long opening, 3 mm wide gap and 5 mm deep;
d. 15 mm long opening, 5 mm wide gap (electrode to electrode) and two temperature sensors mounted on the back wall;
e. 15 mm long opening, 5 mm wide, one 20 mm electrode on one wall and two 5 mm electrodes on second wall with temperature chip between the two smaller electrodes.

These units are machined in two parts from acetyl rod of 11 mm diameter and then bonded together, tapered glue pins being created during this process. Two or three openings to the vacuum are created in the back wall to draw in the tissue. In tests a negative pressure of 0.6 atmospheres was needed to draw tissue into and fill the chamber.

Another device is of a size required to fit down the treatment channel of the endoscope rather than be fixed onto the end of the endoscope. This device also uses a small vacuum chamber but the treatment area/volume is small, with characteristic dimensions of 2 mm. The biopsy port connection acts as the port for the injection of therapeutic agent, a septum being fitted into the biopsy port location tube. This has a major advantage in that the site of injection is also exactly the site of the tissue the treatment of which is enhanced. This septum is necessary to eliminate the need to evacuate the whole biopsy port of the endoscope during application of a vacuum.

In a further embodiment the active elements are interdigitated electrodes so as to launch ultrasonic waves into the tissue.

In a further embodiment the active elements are electrodes configured so as to launch radio-frequency waves into the tissue.

In a further embodiment the active elements are optical wedges configured at the end of an optical fibre or optical fibres so as to evenly illuminate the tissue.

The invention is not limited to the embodiments hereinbefore described, with reference to the accompanying drawings, which may be varied in construction and detail.

The invention claimed is:

1. An apparatus for carrying out electroporation on tissue comprising:
 a housing defining a single vacuum chamber;
 the chamber having an open mouth at a first edge of the chamber, a rear wall, and first and second side walls extending forward from the rear wall to the open mouth;
 a first planar electrode within the chamber, the first planar electrode extending along the first side wall;
 a second planar electrode within the chamber, the second planar electrode extending along the second side wall;
 the first and second planar electrodes extending generally parallel to one another; and
 a vacuum lumen in the housing, the vacuum lumen being in communication with a vacuum source for drawing tissue through the open mouth and into the space within the chamber between the first and second planar electrodes for applying electroporation to tissue within the chamber.

2. The apparatus as claimed in claim 1 wherein the device is configured to define a smooth crossing profile.

3. The apparatus as claimed in claim 1 wherein the chamber comprises a plurality of openings.

4. The apparatus as claimed in claim 1 wherein the apparatus comprises at least one sensor.

5. The apparatus as claimed in claim 4 wherein the apparatus comprises a connector lumen for connecting the sensor in communication with a controller.

6. The apparatus as claimed in claim 1 wherein the device comprises a port to facilitate coupling of an instrument to the device.

7. The apparatus as claimed in claim 6 wherein the instrument is selected from an endoscope, a laparascope, a thorascope, a uretheroscope, and a catheter.

8. The apparatus as claimed in claim 6 wherein the instrument comprises an endoscope.

9. The apparatus as claimed in claim 1 wherein the apparatus comprises a connector lumen for connecting at least one of the electrodes in communication with a controller.

10. The apparatus as claimed in claim 1 wherein the device has a rounded distal end.

11. The apparatus as claimed in claim 1 comprising a needle for injecting a therapeutic agent into tissue.

12. The apparatus as claimed in claim 11 wherein the needle is movable from a retracted position to an extended position.

13. The apparatus as claimed in claim 12 wherein the device comprises a seal or valve for the needle.

14. The apparatus as claimed in claim 1 wherein the chamber comprises a front opening, a rear wall and sides extending between the rear wall and the front opening.

15. The apparatus as claimed in claim 14 wherein the housing comprises a needle opening communicating with the chamber.

16. The apparatus as claimed in claim 15 wherein the needle opening is provided in an end wall of the chamber.

17. The apparatus as claimed in claim 15 comprising a seal or valve for the needle opening.

18. The apparatus of claim 14 wherein the housing comprises an opening at a side of the chamber through which tissue is drawn by an applied vacuum.

19. The apparatus as claimed in claim 1 wherein the rear wall has at least one hole through which a vacuum is applied to draw tissue into the chamber.

20. The apparatus as claimed in claim 19 wherein the rear wall has a plurality of holes therein.

21. The apparatus as claimed in claim 20 wherein the holes lead to a reduced pressure manifold.

22. An apparatus for carrying out electroporation on tissue comprising a device having:
   a housing defining a single vacuum chamber;
   the chamber having an open mouth at a first edge of the chamber, a rear wall, and first and second side walls extending forward from the rear wall to the open mouth;
   a first planar electrode within the chamber, the first planar electrode extending along the first side wall;
   a second planar electrode within the chamber, the second planar electrode extending along the second side wall;
   the first and second planar electrodes extending generally parallel to one another; and
   a vacuum lumen in the housing, the vacuum lumen being in communication with a vacuum source for drawing tissue through the open mouth and into the space within the chamber between the first and second planar electrodes for applying electroporation to tissue within the chamber;
   the device having at least one port to facilitate coupling of an instrument to the device.

23. The apparatus as claimed in claim 22 wherein the instrument is selected from an endoscope, a laparascope, a thorascope, a uretheroscope, and a catheter.

24. The apparatus as claimed in claim 22 wherein the instrument comprises an endoscope.

25. An apparatus for carrying out electroporation on tissue comprising a device having:
   a housing defining a single vacuum chamber;
   the chamber having an open mouth at a first edge of the chamber, a rear wall, and first and second side walls extending forward from the rear wall to the open mouth;
   a first planar electrode within the chamber, the first planar electrode extending along the first side wall;
   a second planar electrode within the chamber, the second planar electrode extending along the second side wall;
   the first and second planar electrodes extending generally parallel to one another; and
   a vacuum lumen in the housing, the vacuum lumen being in communication with a vacuum source for drawing tissue through the open mouth and into the space within the chamber between the first and second planar electrodes for applying electroporation to tissue within the chamber;
   the device comprising a needle for injecting a therapeutic agent into tissue.

26. The apparatus as claimed in claim 25 wherein the needle is movable from a retracted position to an extended position.

27. The apparatus as claimed in claim 25 wherein the device comprises a seal or valve for the needle.

\* \* \* \* \*